United States Patent [19]

Schultz

[11] 4,327,595

[45] May 4, 1982

[54] METHOD AND APPARATUS FOR SIMULTANEOUS DILUTION AND DISPENSATION

[75] Inventor: Harold R. Schultz, Sparks, Nev.

[73] Assignee: Hamilton Company, Reno, Nev.

[21] Appl. No.: 166,141

[22] Filed: Jul. 7, 1980

[51] Int. Cl.³ ............................................. B01L 3/02
[52] U.S. Cl. .............................. 73/864.12; 73/864.17
[58] Field of Search .................. 73/864.12, 864.17; 222/383, 85; 422/100

[56] References Cited

U.S. PATENT DOCUMENTS

| | | | |
|---|---|---|---|
| 2,825,334 | 3/1958 | Kas | 222/85 |
| 3,184,122 | 5/1965 | Nerenberg | 73/864.12 |
| 3,367,746 | 2/1968 | Maurukas | 73/864.12 |
| 3,933,048 | 1/1976 | Scordato | 73/864.17 |

*Primary Examiner*—S. Clement Swisher

*Attorney, Agent, or Firm*—Fitch, Even, Tabin, Flannery & Welsh

[57] ABSTRACT

A method and apparatus for achieving substantially simultaneous dilution or mixing and dispensing is disclosed wherein the diluent or carrier is supplied by a syringe including a relatively large diluent reservoir and a pipette including a replaceable tip for containing a specimen or concentrate, the syringe including a nozzle or tube extending into the interior of the replaceable tip to produce a jet of diluent directed toward an outlet opening formed by the replaceable tip, the specimen being intermixed with the diluent jet for substantially simultaneous dispensation. In a preferred embodiment of the syringe which may be employed by itself or within the above noted diluting dispenser, a replaceable cartridge provides a relatively large volume of the diluent or other material for delivery by the syringe.

30 Claims, 7 Drawing Figures

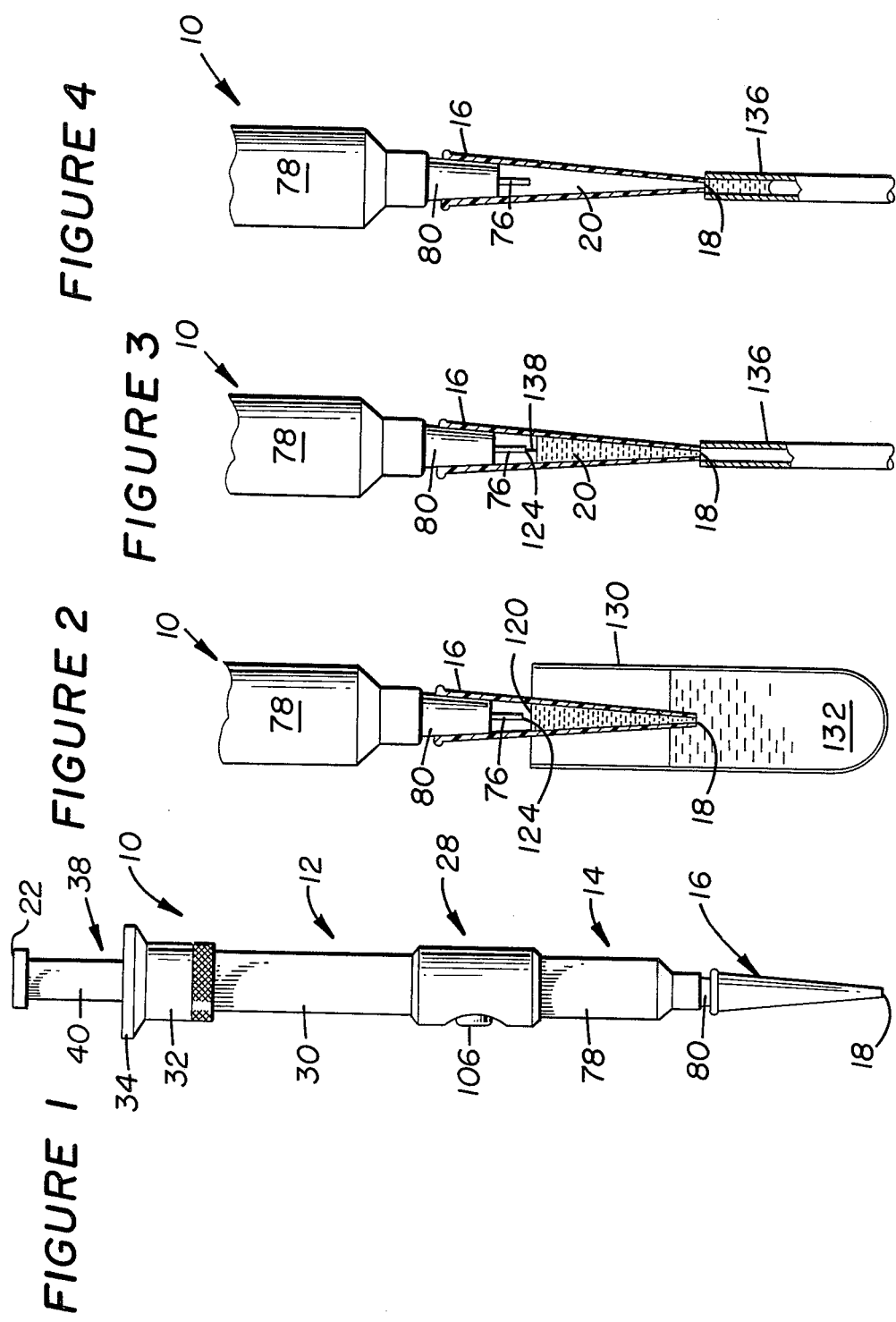

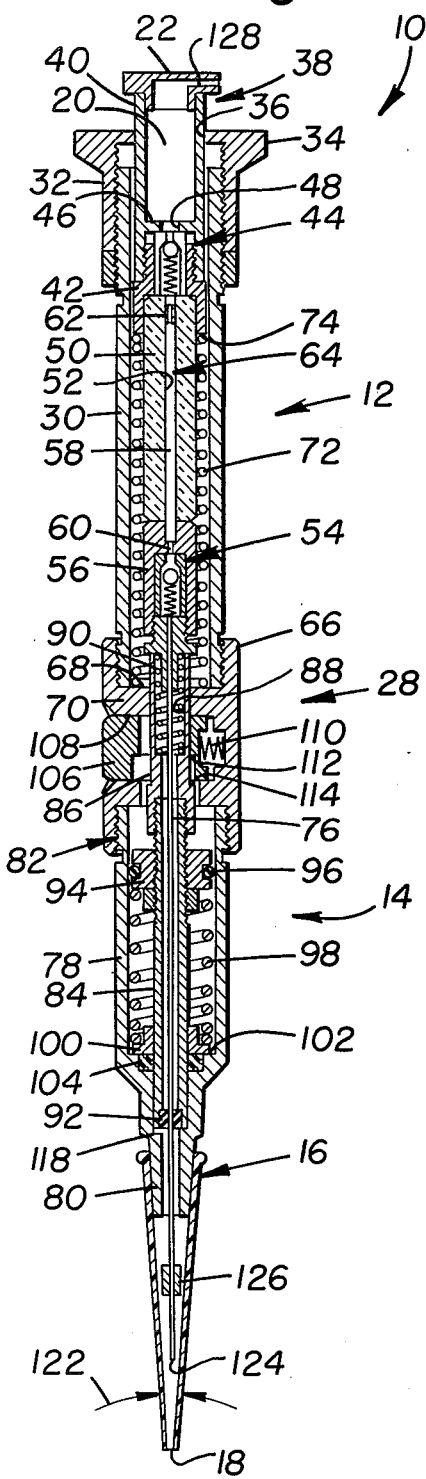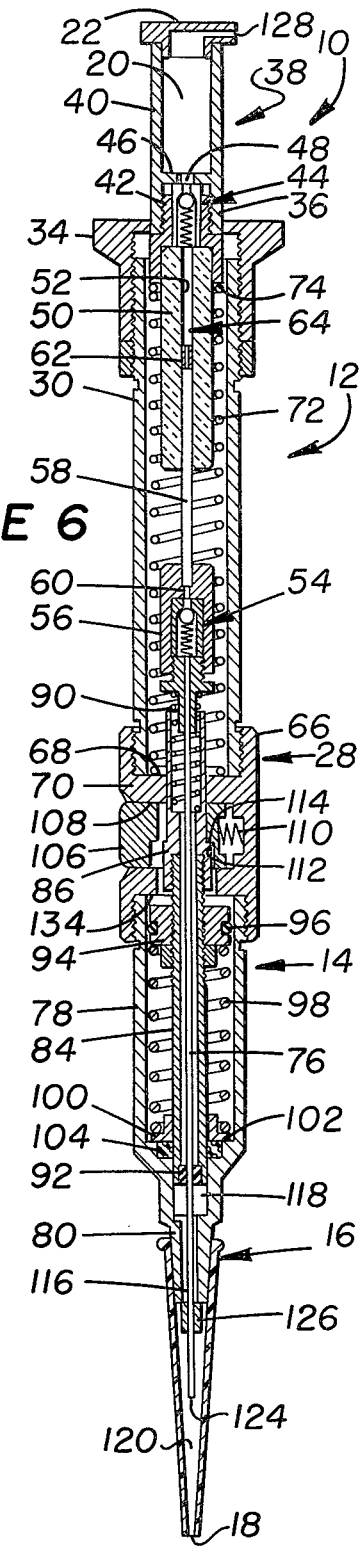

METHOD AND APPARATUS FOR SIMULTANEOUS DILUTION AND DISPENSATION

BACKGROUND OF THE INVENTION

The present invention relates to a method and apparatus for diluting or mixing a specimen or concentrate with a diluent or carrier and substantially simultaneously dispensing the mixture.

In a large number of clinical and analytical techniques employed for example in hospitals, laboratories and the like, it is often necessary to blend or mix a specimen or concentrate with a diluent or carrier. For example, the diluent or carrier may be merely intended to permit proper analysis of the specimen, for example, by extending its effective volume during testing. In other situations, the diluent or carrier may actually interact with the specimen or concentrate in order to condition it for subsequent analysis, evaluation or even for use in medical treatment or the like. Such operations are commonly carried out by means of separate blending and dispensing apparatus or even combined devices where the specimen or concentrate may be blended into the diluent or carrier and subsequently dispensed at a selected rate.

Such techniques have been found to be quite suitable, particularly where the time differential between initial dilution or intermixing of the concentrate and diluent on the one hand and its delivery or dispensation is not critical. However, in a number of applications, it is essential that dispensation of the combined concentrate and diluent occur substantially simultaneously with their intermixing. For example, in many applications, the diluent may react with or otherwise commence conditioning of the concentrate as soon as they come in contact with each other. For applications of this type, it is particularly important that the mixture be dispensed substantially at the same time that it is formed so that further processing is unaffected by initial reaction or conditioning taking place between the concentrate and the diluent. Merely as examples and not to limit the invention, such requirements occur commonly for example in the fields of bioluminescence and chemiluminescence as well as in radioactive immuno assay techniques commonly employed by clinical hospitals.

In order to meet such requirements, relatively complex apparatus and techniques have been employed to assure that mixtures of specimens and diluents are dispensed or available for further processing at substantially the same time they are intermixed. The relative complexity and difficulty of employing such apparatus and techniques has tended to limit their use and also to cause an undesirable delay in many applications where substantially simultaneous dilution and dispensation are required. The use of such apparatus and techniques is even more complex and time consuming when it is necessary to use different materials as one of the dilution components. In such an event, it is commonly necessary to clean substantial portions of the equipment between tests, experiments, etc.

Accordingly, there has been found to remain a need for an efficient method and apparatus for simultaneously diluting and dispensing a combination of a specimen or concentrate and a diluent or carrier.

SUMMARY OF THE INVENTION

It is therefore an object of the present invention to provide a method and apparatus substantially simultaneously diluting and dispensing a specimen or concentrate together with a diluent or carrier, and for overcoming problems of the type described above.

It is a further object of the invention to provide such a method and apparatus permitting variation of one of the dilution materials. For example, in many clinical or analytical techniques, repetitive analyses or experiments may require that a series of specimens or concentrates be combined with the same diluent.

It is an even more specific object of the invention to provide a method and apparatus for achieving simultaneous dilution and dispensation of a specimen or concentrate and a diluent or carrier wherein a predetermined volume of the specimen is drawn into a pipette, a predetermined volume of the diluent being drawn into a syringe or the like and delivered in the form of a jet toward a dispensing opening, the jet interacting with the diluent chamber in order to draw the diluent from the chamber, cause it to be intermixed with the diluent and substantially simultaneously dispensed through a suitable outlet.

More particularly, it is contemplated within the present invention that the jet of diluent pass directly through the specimen chamber toward a restrictive outlet opening. In this manner, the restrictive outlet opening may be sized to normally prevent passage of the specimen, action of the diluent jet causing the specimen to be intermixed therewith and substantially simultaneously carried through the restrictive outlet opening.

In connection with the combination described immediately above, the present invention also contemplates the specimen chamber and outlet opening being formed as a replaceable element. In that manner, the tip may be replaced and a separate specimen may be drawn into the replacement tip without the need for further cleaning. Thus, a number of different specimens may readily be combined with the same diluent and dispensed for further processing or use.

As was also noted above, the invention particularly contemplates that the method and apparatus for achieving substantially simultaneous dilution and dispensation include pipette means for containing the specimen and syringe means for delivering the diluent, the syringe means being employable either individually or with the pipette means and including a replaceable cartridge to provide a relatively large volume of the diluent or other material and at the same time to similarly permit interchange of that component as well. Preferably, the syringe means is of a type including check valves at opposite ends of an expanding and contracting chamber, expansion of the chamber drawing in the diluent or other material and contraction of the chamber causing delivery of the diluent or other material in any manner desired. Within such a combination, the present invention contemplates a replaceable cartridge with means for communicating an interior reservoir volume of the cartridge with the first check valve. Preferably, a housing portion of the syringe may contain the first check valve and a cavity for receiving the replaceable cartridge. Even more preferably, the cartridge may be formed of a penetrable material such as a plastic or rubber, the syringe housing including a needle for penetrating the cartridge to place its interior volume in communication with the first check valve. At the same time, vent means are preferably provided for the reservoir to further facilitate removal of the diluent or other material contained therein.

Additional objects and advantages of the present invention will be apparent from the following description having reference to the accompanying drawings.

BRIEF DESCRIPTION OF THE DRAWINGS

Referring now to the drawings:

FIG. 1 is a side view in elevation of a diluting dispenser of the type contemplated by the present invention.

FIG. 2 illustrates a fragmentary portion of the diluting dispenser of FIG. 1 in an initial step for drawing a specimen into a replaceable tip.

FIG. 3 is a similar fragmentary view illustrating initial formation of a jet of diluent for interacting with the specimen in order to achieve substantial simultaneous dilution or mixing and dispensation into a suitable receiver.

FIG. 4 is a view similar to FIG. 3 illustrating completion of the simultaneous dilution and dispensing step where the respective predetermined volume of the specimen and diluent have been intimately intermixed or diluted and simultaneously dispensed into a receiver.

FIG. 5 is an enlarged view of the diluting dispenser of FIG. 1, with parts being shown in axial section, to better illustrate internal construction thereof, the diluting dispenser of FIG. 5 being illustrated in an operating position after completion of simultaneous dilution and dispensation.

FIG. 6 is a similar view of the diluting dispenser of FIG. 5 in a retracted condition described in greater detail below.

DESCRIPTION OF THE PREFERRED EMBODIMENTS

Figure 7:
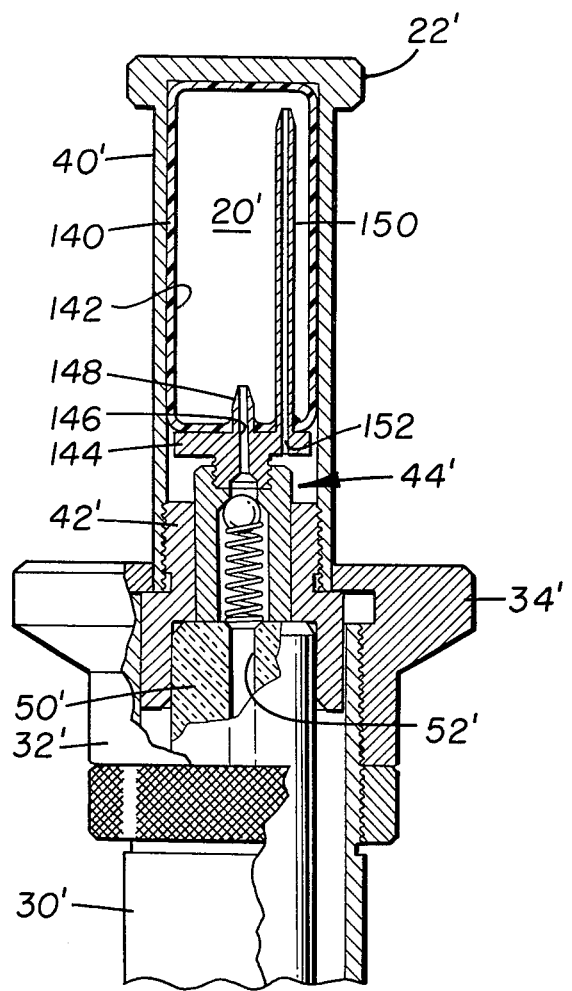
FIG. 7 is a fragmentary view of the upper portion of a diluting dispenser similar to that of FIGS. 5 and 6 while illustrating an alternate embodiment thereof.

Referring now to the drawings and particularly to FIGS. 5 and 6, the apparatus of the present invention is preferably embodied within a diluting dispenser, generally indicated at 10, which is also particularly adapted for performing the method of the invention. In general, the diluting dispenser 10 has a syringe portion 12 at its upper end for containing and supplying a diluent or carrier, the lower end of the dispenser 10 comprising an air type pipette including a replaceable tip for containing a predetermined volume of a selected specimen or concentrate.

Before proceeding with a detailed description of the diluting dispenser 10 and its method of operation, the present invention may generally be summarized as follows. The diluting dispenser 10 is contemplated as a preferred means for substantially simultaneously diluting and dispensing predetermined volumes of a specimen and diluent. As will be described in greater detail below, the syringe 12 is operated to prepare a predetermined volume of the diluent, combined operation of the syringe and pipette functioning in a manner also described in detail below for drawing a predetermined volume of a specimen or the like into a replaceable tip 16. The syringe 12 is then operated in order to produce a jet of the diluent directed toward an outlet or dispensing opening 18 formed by the replaceable tip 16. Interaction of the jet with the specimen causes the specimen to be drawn into and mixed or diluted with the diluent, the mixture or dilution being substantially simultaneously dispensed or propelled through the opening 18 for further processing or use.

This combination of features within the diluting dispenser 10 and the corresponding method of operation comprise one portion of the invention. In particular, the invention is concerned with the method and apparatus for producing interaction between the jet of diluent and the specimen contained in its chamber for producing substantially simultaneous dilution or mixing and dispensation.

As will also be described in greater detail below, the syringe portion 12 of the diluting dispenser 10 is contemplated to include a reservoir 20 for containing a relatively large volume of diluent in order to facilitate repeated operations on the diluting dispenser 10. As illustrated in FIGS. 5 and 6, a cap 22 for the reservoir may be removed in order to replenish the reservoir supply of diluent. However, the invention also contemplates another possible construction for the reservoir as may be seen in the alternate embodiment of FIG. 7. In FIG. 7, those portions of the diluting dispenser which correspond to similar portions of the dispenser in FIG. 5 are illustrated by similar primed numerals. Referring now to FIG. 7, it may be seen that the reservoir 20 is formed by a replaceable cartridge 24 preferably constructed of penetrable material such as an elastomer or plastic for example, the diluting dispenser 10' including means in the form of a needle 26 for penetrating the cartridge in order to permit the diluent to be drawn therefrom during operation of the dispenser 10'.

At the same time, the invention contemplates a method for operation of a diluting dispenser such as that illustrated at 10 and 10' in the drawings as well as a method for simultaneously diluting and dispensing a combination of a specimen and diluent by propelling a jet of the diluent toward an outlet opening and causing it to interact with a predetermined volume of the specimen whereby the specimen is drawn toward the jet, diluted or intermixed therewith and simultaneously dispensed. The apparatus and method of the present invention, as summarized above, are described in greater detail below.

Referring now to FIGS. 5 and 6, construction and operation of the diluting dispenser 10 may be best understood by considering its separating operating portions. In addition to the syringe portion 12 and air pipette portion 14 as noted above, the diluting dispenser 10 also includes a latch portion 28 which is described in greater detail below following a description of the pipette portion 14 with which is cooperates.

Initially, the syringe portion 12 includes a cylindrical housing 30 which is threadedly engaged at its upper end with a flanged adapter 32. The flanged end 34 of the adapter forms an opening 36 permitting reciprocating movement of a plunger assembly 38. The plunger assembly 38 includes at its upper end a cylinder 40 which in turn is closed by the cap 22 to form the reservoir 20. At its lower end, the cylinder 40 is threaded into a housing 42 containing a first check valve assembly 44. A radially extending wall 46 at the lower end of the cylinder 40 completes the enclosure for the reservoir 20 and forms an opening 48 for communicating the reservoir 20 with the first check valve assembly 44.

The housing 44 at its lower end is secured to a tubular extension 50 forming a small axially arranged bore 52 along its length. A second check valve assembly 54 is contained within a housing 56 generally toward the opposite end of the cylindrical housing 30. A tubular plunger 58 is secured to the housing 56 and is in communication with the second check valve assembly 54 by means of a passage 60 formed in the housing 56. The plunger 58 has an outside diameter slightly smaller than the diameter of the bore 52 in order to permit reciprocating movement of the plunger 58 within the bore 52. A tubular sealing tip 62 is secured to the upper end of the plunger 58 in order to permit communication between the bore 52 and the interior of the tubular plunger 58 while providing a sliding seal against the surface of the bore 52. In this manner, the bore 52 and the plunger 58 serve to form a closed diluent chamber between the check valve assemblies 44 and 54, the length and effective volume of the diluent chamber, generally indicated at 64 being variable as the housing 56 and plunger 58 move within the outer cylindrical housing 40 in a manner to be described below.

As was also noted above, the lower end of the cylindrical housing 30 is threaded into an intermediate housing 66 for the latch portion 28 of the dispenser 10. An upper surface 68 of a radially extending wall portion 70 of the housing 66 forms a stop surface for a spring 72 arranged in the annular space between the housing 30 and either the check valve housing 56 or tubular extension 50. The upper end of the spring 72 acts against the lower end 74 of the first check valve housing 42. Accordingly, the check valve housing 42, the tubular extension 50 and the reservoir cylinder 40 are normally extended upwardly into the position illustrated in FIG. 6. At the same time, upward travel of the second check valve assembly housing 56 is limited in a manner described in greater detail below.

Generally, the components in the lower portion of the dispenser 10 may be considered part of the air pipette portion 14 except for a long jet tube 76 which is secured at its upper end to the second check valve assembly housing 56 and extends downwardly through the length of the air pipette portion 14 and into the replaceable tip 16. The upper end of the jet tube 76 is also in communication with the second check valve assembly 54. Accordingly, when the second check valve assembly 54 is in an open position, the jet tube 76 is placed in communication with the diluent chamber 64 formed by the tubular plunger 58 and bore 52.

The air pipette portion 14 of the dispenser 10 is arranged within a cylindrical housing 78 which is generally closed at its lower end 80, its upper end being threaded into the intermediate housing 66 as generally indicated at 82. A tubular air piston 84 extends through a substantial portion of the interior of the pipette housing 78 while being threaded into engagement at its upper end with a cylindrical adapter 86. The upper end of the cylindrical adapter 86 is formed with a counter bore 88 to receive a spring 90 arranged for compression interaction between the adapter 86 and the second check valve housing 56. As illustrated in FIG. 5, the cylindrical adapter 86 is illustrated with its upper end in contact with the second check valve assembly housing 56. However, separation between the housing 56 and cylindrical adapter 86 is contemplated during operation of the dispenser, as is illustrated for example in FIG. 6, for allowing proper operation both of the syringe portion 12 and the air pipette portion 14. It may also be seen from FIGS. 5 and 6 that the jet tube 76 passes through the interior of both the tubular air piston 84 and the cylindrical adapter 86. The lower end of the tubular air piston 84 is also formed with a counter bore to receive a seal member 92 which forms a sliding seal with the jet tube 76.

A nut 94 is also threaded to the tubular air piston 84 adjacent its upper end and includes an O-ring 96 mounted for sealing engagement with the inside surface of the cylindrical housing 78. A relatively strong spring 98 is arranged for interaction in compression between the nut 94 and a spring adapter 100 resting upon a shoulder 102 formed by the cylindrical housing 78. The adapter 102 is sized to permit relative movement of the tubular air piston 84 therethrough while a seal is formed between the tubular air piston 84, the adapter 100 and the pipette housing 78 by means of a low friction O-ring 104. Thus, the spring 98 tends to urge the nut 94, the air piston 84 and the cylindrical adapter 86 upwardly. In the position illustrated in FIG. 5, upward travel of those components is limited by interaction between the upper end of the cylindrical adapter 86 and the second check valve assembly housing 56. However, it may also be seen from FIG. 6 that separation is contemplated between the second check valve assembly housing 56 and the cylindrical adapter 86.

The purpose for this operating feature, which is described in greater detail below, will be further apparent in connection with the following description of the latch portion 28. The latch portion 28 includes a manual latch element or button 106 which is arranged in a laterally extending passage 108 formed by the housing 66. The latch element 106 is urged in a leftward direction, as viewed in FIG. 5, by means of a spring 110. The latch element 106 encompasses the cylindrical adapter 86 and forms a latching or stop surface 112 which is arranged for selective engagement with a shoulder 114 formed on the cylindrical adapter 86. The manner in which the components described above function will be more apparent with the following operating description.

Before describing the mode of operation for the dispenser 10, it is also noted that the lower end 80 of the cylindrical housing 78 forms a passage 116 through which the jet tube 76 extends into the replaceable tip 16. The interior of the lower cylindrical housing end 80 forms an aspirating chamber 118 which is closed at its upper end by the seal 92 and the tubular air piston 84. Relative expansion and contraction of the aspirating chamber 118 may be seen for example by comparison of FIGS. 5 and 6. Otherwise, the lower end 80 of the cylindrical housing 78 provides a press-fitting mount for the replaceable tip 16. As is illustrated in FIGS. 5 and 6 and as may also be seen in FIGS. 1–4, the outlet or dispensing opening 18 at the lower end of the tip 16 forms a restrictive passage in communication with the interior 120 of the tip which forms a chamber for receiving a specimen or concentrate as will also be described in greater detail below. The relative size of the outlet opening 18 especially in comparison with the size of the jet tube 76 is of importance to the present invention as is the tapered configuration for the interior 120 of the tip. In this regard, the jet tube 76 is formed with a passage having a maximum size of no more than approximately the diameter of the outlet passage 18. As will be apparent from the following operating description, this relation is important in order that a diluent jet formed by the tube 76 may pass relatively freely through the tip 16 without encountering the interior walls of the tip. At the same time, the interior surface of the tip 16 is gradually tapered so that the diluent jet passing from the tube 76 will tend to draw the specimen from the interior of the tube, causing the specimen to be diluted within the diluent jet and at the same time carried out of the opening 118. For this reason, the enclosed angle formed by the tapered interior of the tube 16 is an acute angle, preferably of no more than approximately 30° and even more preferably within the range of approximately 5°–15° as is illustrated in the drawings. The enclosed angle for the interior of the tip 16 is indicated for example in FIG. 5 at 122. In the present embodiment, the outlet opening 18 has a diameter of 0.05 centimeters while the inside diameter of the jet tube 76 is 0.04 centimeters.

It may be further seen, particularly in FIGS. 5 and 6, that the lower end of the jet tube 76 extends downwardly into the interior of the replaceable tip 16. Preferably, as will also be described below in connection with FIGS. 1–4, it is particularly contemplated that the lower end 124 of the jet tube remain closely adjacent the upper surface of the specimen or concentrate contained within the tip 16. Further in this regard, it may also be seen by comparison of FIGS. 5 and 6 that the jet tube moves downwardly through the tip as the diluent jet is being directed through the tip, carrying with it the specimen originally contained within the tip. A stop member 126 is secured to the jet tube 76 which always permits free communication between the interior of the tip and the aspirating chamber 118. The purpose of the stop member 126 is to limit upward travel of the housing 56 for the second check valve assembly. In this manner, the stop member 126 acts against the end 80 of the pipette housing 78 to limit upward travel of the second check valve housing 56 and thus establish normal maximum volume for the diluent chamber 64.

Before proceeding with a description of the mode of operation for the diluting dispenser of FIGS. 1–6, it is noted that during operation, diluent is drawn from the reservoir 20. In order to permit the diluent to continuously flow from the reservoir and to prevent collapse of the reservoir, a vent 128 is provided in the cap 22 for the reservoir.

It is believed that the mode of operation for the diluting dispenser 5 will be obvious from the preceding description. However, operation is described in some detail below since the method of operation for the diluting dispenser 10 and particularly the manner in which the dispenser function to form a jet of diluent for carrying a specimen from the tip 16 are important features of the invention.

The method of operation for the diluting dispenser 10 may be best seen by combined reference to FIGS. 5 and 6 along with FIGS. 1–4. In FIG. 1, the diluting dispenser is illustrated in a retracted position corresponding to that of FIG. 6. As may be seen in FIG. 6, the plunger assembly 38 is retracted so that diluent from the reservoir 20 flows into the diluent chamber 64 formed by the bore 52 and plunger 58. However, the diluting dispenser 10 is also adapted to provide a predetermined volume of a specimen or concentrate within the replaceable tip 16.

In order to draw the specimen into the tip, having reference to FIG. 2, the opening 18 of the tip is immersed in a vial 130 containing a relatively large quantity 132 of the specimen. With the tip of the diluting dispenser 10 immersed in the specimen, the latch button 106 is depressed, thereby shifting the latch surface 112 and releasing the shoulder 114 of the cylindrical adapter 86. Thereupon, the adapter 86, the tubular air piston 84 and the nut 94 are forced upwardly by the spring 98 in order to expand the aspirating chamber 118, producing a vacuum within the interior specimen chamber 120 of the tip and drawing a predetermined volume of the specimen 132 into the tip. The predetermined volume of relative expansion for the aspiration chamber 118, which in turn determines the amount of specimen drawn into the tip, is established by travel of the air piston 84 which is limited by interaction of the nut 94 with a stop surface 134 formed by the intermediate housing 66.

The spring 98 is relatively strong in order to assure proper positioning of the air piston 84 and adapter 86, normally in engagement with the second check valve assembly housing 56 (see FIG. 5). At the same time, it is desirable that the rate of evacuation formed within the tip interior 120 by the aspirating chamber 118 develop relatively slowly in order to prevent air from being drawn into the tip. Accordingly, the O-ring 96 is arranged for engagement with the interior of the cylindrical housing 78 in order to produce a dashpot effect for regulating the rate of travel for the nut 94, the air piston 84 and the adapter 86. Thus, after release of the detent or latch button 106, the diluting dispenser 10 assumes the position described above as illustrated in FIG. 2 with a predetermined volume of the specimen contained within the interior 120 of the tip 16.

Thereafter, the diluting dispenser is positioned with the dispensing opening 18 of the tip in a suitable receiver 136 into which the mixture of the specimen 132 and diluent are to be dispensed. With the diluting dispenser in position as illustrated in FIG. 3, the plunger assembly 38 is depressed, thereby foreshortening the diluent chamber 64 and causing the diluent to flow through the second check valve assembly 54 and through the jet tube 76 in order to form a jet 138 of diluent projected by the jet tube 76 toward the dispensing opening 18. At the same time, the diluent jet 138 is caused to interact with the specimen contained within the tip. Preferably, the jet 138 is directed through the axial center of the interior volume of the tip containing the specimen thereby creating a turbulent flow condition surrounding the jet as it passes toward the dispensing opening 18. It is believed that the specimen is drawn into the diluent jet, primarily by frictional effects of the turbulent region about the jet so that the specimen is intimately intermixed with the diluent and at the same time carried toward and through the dispensing opening 18. As is illustrated in each of FIGS. 2 and 3, the lower end of the jet tube 76 is closely adjacent to but in spaced apart relation from the surface of the specimen within the tip interior 120 prior to dispensing operation of the diluting dispenser 10. As may also be seen by comparison of FIGS. 5 and 6, the lower end of the jet 76 travels downwardly through the tip interior during dispensing operation. Thus, the tip remains generally adjacent the surface of the specimen as it is drawn into the diluent jet and carried out of the dispensing opening 18. With the plunger assembly 38 being fully depressed into the dispenser 10, as is illustrated in FIG. 5, the diluent is evacuated from the diluent chamber 64 and the specimen is entirely removed from the interior 120 of the tip 16. Thus, the predetermined volume of the specimen and diluent are simultaneously intermixed and dispensed into the receiver 136.

Air expelled from aspirating chamber 118 serves at least to prevent formation of a vacuum within the tip 16. Preferably air from 118 assures that the total volume of specimen is expelled in intermixed form with the diluent from chamber 120 of the tip.

After complete dispensation of the mixture or dilution, the plunger assembly 38 is released and returned to its retracted position under the influence of the spring 72. As the plunger assembly is retracted in this manner, it expands the volume of the diluent chamber 64, thus causing a fresh predetermined volume of the diluent to be drawn into the diluent chamber 64 from the reservoir 20. The vent 128 of course permits air to enter the reservoir in order to prevent development of a vacuum within the reservoir to interfere proper operation of the dispenser. As the plunger assembly 38 is returned by its spring, the second check valve assembly housing 56, the cylindrical adapter 86, the tubular air piston 84 and the nut 94 are freed to rise or retract under the influence of the spring 98. However, upward travel of the adapter 86 is limited by interaction of the shoulder 114 with the stop surface 112 on the detent button 106. Thus, upward travel of the nut 94 and the air piston 84 and adapter 86 which are interconnected therewith is arrested in the position illustrated in FIG. 6. The second check valve assembly housing 56 is urged further upwardly within the cylindrical housing 30 by the spring 90. This arrangement permits a lost motion connection between the second check valve assembly housing 56 and the cylindrical adapter 86 which prevents interference with the volume of the diluent chamber 64 upon operation of the detent button 106. As seen in FIG. 6, the spacing between the second check valve assembly housing 56 and the cylindrical adapter 86 corresponds to the spacing between the nut 94 and the stop surface 134 on the intermediate housing 66. Thus, when the detent button 106 is again depressed in order to draw a fresh supply of specimen into the interior 120 of the tip, those components are urged upwardly by the spring 98 so that the cylindrical adapter 86 just enters into engagement with the second check valve housing 56 as the nut 94 engages the stop surface 124. Thus, with those components in contact, the entire dispenser is again conditioned to repeat the dispensing operation described above.

However, before the detent button 106 is again depressed, the tip 16 may be replaced and immersed into a different supply of specimen when a different analytical or clinical evaluation or procedure is contemplated or to merely prevent cross-contamination between successive specimens. Thus, the diluting dispenser 10 is particularly adapted to facilitate simultaneous intermixing and dispensing of each of a number of different specimens.

At the same time, it is particularly contemplated that the same diluent be supplied from the reservoir 20. However, it is also contemplated in connection with the embodiment of FIG. 7 as described below that the diluent reservoir may be formed by a replaceable and/or disposable cartridge 140 in order to also permit selective rapid replacement or replenishing of the diluent. In any event, before describing the alternate embodiment of FIG. 7, it may be seen from the preceding operating description that the diluting dispenser is particularly adapted to facilitate simultaneous intermixing and dispersing of one or more specimens together with one or more diluents in a single procedure or in multiple operations.

Referring now to FIG. 7, the cylindrical housing 40' is formed with a cavity 142 adapted to receive the replaceable cartridge 140. The replaceable cartridge 140 is preferably formed from a penetrable material such as an elastomer or plastic, its interior forming the reservoir 20' for containing a supply of the diluent. The first check valve assembly 44' is slightly modified from what was described and illustrated in connection with FIGS. 5 and 6 in that an adapter plate 144 is attached to the housing 42' while forming an opening 146 in communication with the first check valve assembly 44'. At the same time, a first needle 148 arranged in communication with the opening 146 extends upwardly from the plate 144 in order to penetrate the cartridge 140 as it is installed within the cavity 142 and to place the reservoir 20' in communication with the first check valve assembly 44'. At the same time, a substantially longer second needle 150 is also mounted upon the adapter plate 144 and similarly penetrates the replaceable cartridge 140 and extends closely adjacent the upper end thereof. The second needle 150 is also in communication with a vent passage 152 formed by the plate 144 to provide a vent for the reservoir 20' in substantially the same manner as the vent 128 in FIGS. 5 and 6.

In FIG. 7, the housing 40' is illustrated for threaded engagement with the housing 42' for the first check valve assembly 44'. However, the cylinder 40' could also have a threaded cap similar to the cap 22 illustrated in FIGS. 5 and 6. At the same time, it would also be possible to form the cylinder 40 merely with an opening at the top so that the cartridge 140 could be forced downwardly into the cavity 142 to be penetrated by the needles 148 and 150. With such an arrangement, manual depression of the plunger assembly 38' would then be accomplished by pressing directly on the top of the disposable cartridge 140 which would serve to maintain it in engagement with the adapter plate 144.

Accordingly, there has been described a method and apparatus for simultaneously intermixing and dispensing a specimen and diluent from a diluting dispenser of the type illustrated at 10 in FIGS. 5 and 6 or at 10' in FIG. 7. At the same time, there has been illustrated and described a novel method and apparatus for producing simultaneous intermixing and dispensing in the form of the diluent jet directed toward an outlet opening and at the same time arranged for interaction with a predetermined volume of the specimen. Finally, there has also been described and illustrated a novel cartridge replacement for a syringe which may either be employed by itself or in combination with a diluting dispenser of the type illustrated either at 10 in FIGS. 1–6 or at 10' in FIG. 7.

Numerous variations and modifications will be apparent from the preceding description. For example, a number of different dispensing devices may be employed to produce the diluent jet described for interacting and intermixing with the specimen while simultaneously dispensing the mixture. Other arrangements for drawing the specimen into the diluent jet may also be employed within the diluting dispenser of FIGS. 5 and 6. For example, rather than directing the diluent jet to pass through the specimen, the jet could for example be produced by passage through a venturi arrangement including a side arm in connection with a low pressure restriction in the venturi. With such an arrangement, the specimen could be placed in a specimen chamber in communication with the side arm to be drawn into the restrictive passage of the venturi by action of the jet, intimate intermixing resulting therein with the mixture or dilution substantially simultaneously being dispensed from the device.

It will be apparent that the diluting dispenser described above can also be used for simple dilution procedures regardless of whether simultaneous dispensation is required or not. In addition, the dispenser may also be used for dispensing materials which are not susceptible to being retained within the tip 16 by surface tension in the manner described above. For example, if the specimen where of a type having insufficient surface tension for retention within the tip, the restrictive opening 18 could be adapted to include valve means for containing the specimen while being responsive to the diluent jet for opening and permitting passage of the intermixed jet of diluent and specimen.

Similarly, various other features of the method and apparatus of the invention could be modified within the scope of the present invention. Accordingly, the scope of the present invention is defined only by the following appended claims.

What is claimed is:

1. A diluting dispenser for mixing a specimen with a diluent and substantially simultaneously dispensing the mixture, comprising
    syringe means including a diluent chamber, and means for drawing a predetermined volume of the diluent into said diluent chamber and for expelling the diluent from said diluent chamber, and
    pipette means including a dispensing tip, a specimen chamber and means for drawing a predetermined volume of the specimen into said specimen chamber,
    said diluent expelling means including nozzle means directed toward said dispensing tip and arranged for interaction with said specimen chamber in order to draw said specimen into intimately mixed relation with a jet of diluent as it passes toward said dispensing tip so that the mixture of diluent and specimen is dispensed substantially simultaneously as it is mixed,
    said syringe means further comprising a reservoir from which diluent is drawn into said diluent chamber, the means for drawing a predetermined volume of diluent into said diluent chamber comprising a first check valve communicating said diluent reservoir with said diluent chamber and a second check valve communicating said diluent chamber with said nozzle means, said means for drawing diluent into said diluent chamber and for expelling diluent from said diluent chamber comprising means for effectively expanding and contracting said diluent chamber.

2. The diluting dispenser of claim 1 further comprising vent means for said reservoir.

3. The diluting dispenser of claim 1 wherein said nozzle means comprises an elongated tube extending from said second check valve toward said dispensing tip.

4. The diluting dispenser of claim 1 wherein said means for drawing specimen into said specimen chamber comprises spring-loaded means forming an aspiration chamber in communication with said specimen chamber.

5. The diluting dispenser of claim 4 wherein said spring-loaded means is shifted in a direction to contract said aspirating chamber by said means for expelling diluent from said diluent chamber.

6. The diluting dispenser of claim 5 further comprising latch means for maintaining said spring-loaded member in said contracted position and means for selectively releasing said latch in order to permit movement of said spring-loaded member under its spring load in order to expand said aspirating chamber and thereby draw the specimen into said specimen chamber.

7. The diluting dispenser of claim 6 wherein said nozzle means comprises an elongated tube extending from said second check valve toward said dispensing tip, said aspirating chamber being annularly formed about said elongated tube.

8. A diluting dispenser for mixing a specimen with a diluent and substantially simultaneously dispensing the mixture, comprising
    syringe means including a diluent chamber, and means for drawing a predetermined volume of the diluent into said diluent chamber and for expelling the diluent from said diluent chamber, and
    pipette means including a dispensing tip, a specimen chamber and means for drawing a predetermined volume of the specimen into said specimen chamber,
    said diluent expelling means including nozzle means directed toward said dispensing tip and arranged for interaction with said specimen chamber in order to draw said specimen into intimately mixed relation with a jet of diluent as it passes toward said dispensing tip so that the mixture of diluent and specimen is dispensed substantially simultaneously as it is mixed, said means for drawing specimen into said specimen chamber comprising spring-loaded means forming an aspiration chamber in communication with said specimen chamber, wherein said spring-loaded means is shifted in a direction to contract said aspirating chamber by said means for expelling diluent from said diluent chamber.

9. The diluting dispenser of claim 8 further comprising latch means for maintaining said spring-loaded member in said contracted position and means for selectively releasing said latch in order to permit movement of said spring-loaded member under its spring load in order to expand said aspirating chamber and thereby draw the specimen into said specimen chamber.

10. The diluting dispenser of claim 1 wherein said diluent reservoir is formed by an element which is replaceably arranged within the diluting dispenser for communication with said first check valve.

11. The diluting dispenser of claim 10 wherein the diluting dispenser further comprises means for receiving the replaceable element and means for communicating said diluent reservoir formed by said replaceable element with said first check valve.

12. The diluting dispenser of claim 11 wherein said replaceable element is formed from a penetrable material, said means for communicating said diluent reservoir with said first check valve comprising a needle arranged for penetrating said replaceable element when it is mounted within said diluting dispenser.

13. The diluting dispenser of claim 12 further comprising additional means for venting said diluent reservoir.

14. A diluting dispenser for mising a specimen with a diluent and substantially simultaneously dispensing the mixture, comprising
    syringe means including a diluent chamber, and means for drawing a predetermined volume of the diluent from said diluent chamber, and
    pipette means including a dispensing tip, a specimen chamber and means for drawing a predetermined volume of the specimen into said specimen chamber,
    said diluent expelling means including nozzle means directed toward said dispensing tip and arranged for interaction with said specimen chamber in order to draw said specimen into intimately mixed relation with jet of diluent as it passes toward said dispensing tip so that the mixture of diluent and specimen is dispensed substantially simultaneously as it is mixed, said syringe means further comprising a reservoir from which diluent is drawn into said diluent chamber, wherein said diluent reservoir is formed by an element which is replaceably arranged within the diluting dispenser for communication with said means for drawing diluent into said diluent chamber.

15. The diluting dispenser of claim 14 wherein said diluting dispenser further comprises means for receiving the replaceable element and means for communicating said diluent reservoir formed by said replaceable element with said means for drawing diluent into said diluent chamber.

16. The diluting dispenser of claim 15 wherein said replaceable element is formed from a penetrable material, said means for communicating said diluent reservoir with said means for drawing diluent into said diluent chamber comprising a needle arranged for penetrating said replaceable element when it is mounted within the diluting dispenser.

17. The diluting dispenser of claim 16 further comprising additional means for venting said diluent reservoir.

18. A diluting dispenser for substantially simultaneously mixing a specimen with a diluent and dispensing the mixture, comprising a dispensing tip forming a restrictive opening for dispensing the mixture, means forming a specimen chamber in communication with said opening and means for directing a jet of the diluent into the specimen and toward said restrictive opening of the dispensing tip in order to draw the specimen into intermixed relation with the diluent jet for dispensation through said restrictive opening, the specimen being a liquid and said restrictive opening being sized to permit the specimen to be drawn into the specimen chamber and to permit passage of the jet of diluent and intermixed specimen, surface tension of the specimen normally preventing its passage through said restrictive opening, wherein an interior surface of said replaceable element tapers outwardly and longitudinally away from said restrictive opening to form said specimen chamber, said jet directing means comprising tubular means extending into the interior of said replaceable element in facing relation with said restrictive opening.

19. The diluting dispenser of claim 18 further comprising a housing including said jet directing means, said dispensing tip being a replaceable element secured to the housing, an interior portion of the replaceable element forming the specimen chamber.

20. The diluting dispenser of claim 18 wherein said restrictive opening includes means for normally preventing passage of said specimen therethrough while permitting passage of a jet of diluent and intermixed specimen.

21. The diluting dispenser of claim 18 wherein said tubular means is adapted for movement within said replaceable element toward said restrictive opening while directing the jet of diluent into the specimen so that a projecting end of said tubular means remains in closely spaced apart relation to specimen remaining within said specimen chamber.

22. The diluting dispenser of claim 18 wherein the tubular means is sized relative to the size of said restrictive opening and the tapered interior of said replaceable element to facilitate blending of the concentrate with the diluent and passage of the resulting mixture through said restrictive opening.

23. The diluting dispenser of claim 22 wherein the interior of said replaceable element is formed with a taper having a maximum enclosed angle of about 30°.

24. The diluting dispenser of claim 23 wherein the interior of the replaceable element is tapered to form an included angle approximately within the range of 10°–15°.

25. The diluting dispenser of claim 18 wherein said jet directing means is sized relative to the size of said restrictive opening and configuration of said specimen chamber for facilitating intermixing of specimen with said diluent jet and for facilitating passage of said mixture through said restrictive opening.

26. In a method for mixing a specimen with a diluent and substantially simultaneously dispensing the mixture, the steps comprising
drawing a predetermined volume of the diluent into a diluent chamber formed by a syringe means,
drawing a predetermined volume of the specimen into a specimen chamber,
expelling the diluent from the diluent chamber and forming a diluent jet directed toward a dispensing tip while interacting the jet with the specimen in the specimen chamber in order to draw the specimen into intimately mixed relation with the diluent jet as it passes toward said dispensing tip so that the mixture of diluent and specimen is dispensed substantially simultaneously as it is mixed, and
further comprising the step of providing pipette means for drawing the predetermined volume of specimen into the specimen chamber, cocking the pipette into a latched condition and against a spring-load by action of the syringe means and subsequently unlatching the pipette in order to draw the predetemined volume of specimen into the specimen chamber.

27. The method of claim 26 further comprising the step of providing a replaceable tip on the pipette means, the replaceable tip forming a dispensing opening and an interior chamber for receiving the specimen.

28. In a method for substantially simultaneously mixing a specimen with a diluent and dispensing the mixture, the steps comprising
arranging a predetermined volume of the specimen in a specimen chamber in communication with a restrictive dispensing opening, and
directing a jet of the diluent into the specimen and toward said restrictive opening in order to draw the specimen into intermixed relation with the diluent jet for simultaneous dispensation through said restrictive dispensing opening, further comprising the step of introducing fluid into the specimen chamber along with the diluent jet to assist in expelling the specimen and diluent from the specimen chamber.

29. The method of claim 28 further comprising the step of introducing the diluent jet into the specimen chamber through a tube which is movable through the chamber to remain generally closely adjacent the specimen.

30. The method of claim 28 wherein the fluid is air.

* * * * *